United States Patent [19]

Geerlings et al.

[11] Patent Number: 5,246,691
[45] Date of Patent: Sep. 21, 1993

[54] RADIOIMMUNOTHERAPY USING α-PARTICLES EMISSION

[75] Inventors: Maurits W. Geerlings, Rozendaal; Franciscus M. Kaspersen, Heesch, both of Netherlands

[73] Assignee: Akzo N.V., Arnhem, Netherlands

[21] Appl. No.: 657,580

[22] Filed: Feb. 19, 1991

[30] Foreign Application Priority Data

Jun. 19, 1989 [EP] European Pat. Off. ....... 89.201591.8
Jun. 19, 1990 [WO] PCT Int'l Appl. ............. PCT/EP90/00990

[51] Int. Cl.$^5$ ................. A61K 43/00; C07F 17/00
[52] U.S. Cl. ................................. 424/1.1; 534/10
[58] Field of Search ..................... 424/1.1; 534/10

[56] References Cited

U.S. PATENT DOCUMENTS

| | | |
|---|---|---|
| 4,454,106 | 6/1984 | Gansow et al. ............. 424/1.1 |
| 4,472,509 | 9/1984 | Gansow et al. ............. 424/1 |
| 4,816,397 | 3/1989 | Boss et al. |
| 4,828,991 | 5/1989 | Hanna et al. |
| 4,923,985 | 5/1990 | Gansow et al. ............. 540/474 |

OTHER PUBLICATIONS

Scheinberg et al, "Targeting in Erythroleukemic Mice . . .," *Monoclonal Antibodies Drug Dev.*, Process John Jacob Abel Symp. for Drug Dev. 1982, pp. 159–171.

"Astatine-211: It's Possible Applications in Cancer Therapy", Brown, *International Journal of Radiation Applications and Instrumentation* Part A, vol. 37, No. 8, pp. 789–798 (1986).

"Preparation of $^{224}$Ra for Therapy of Ankylosing Spondylitis", Delikan *Health Physics*, vol. 35, No. 1, pp. 21–24 (1978).

*Primary Examiner*—Robert L. Stoll
*Assistant Examiner*—Matthew Zmurko
*Attorney, Agent, or Firm*—William M. Blackstone

[57] ABSTRACT

The present invention relates to the use of Actinium or one of its daughters in radioimmunotherapy. Also provided are immunoconjugates comprising an isotope, a chelating agent and a slowly localizing antibody. The invention also includes pharmaceutical compositions comprising said immunoconjugates, as well as such compositions comprising one or more scavenging agents. The compositions according to the invention are particularly useful for the treatment of micrometastases in adjuvant therapy, as well as for treatment of localized tumors.

6 Claims, No Drawings

RADIOIMMUNOTHERAPY USING α-PARTICLES EMISSION

This invention generally relates to immunotherapy using radionuclides. More specifically it relates to immunotherapy using radionuclides which emit α-particles (Helium-nuclei).

BACKGROUND OF THE INVENTION

This invention also relates to a radioimmunoconjugate comprising a radionuclide that emits α-particles, a chelating agent and an antibody specific for tumor associated antigens.

Radionuclides that emit α-particles have a number of physical characteristics that make them attractive for radioimmunotherapy.

The range of an α-particle with an energy of 5 to 8 MeV is in the order of 40 to 80 αm, which limits their effectiveness to a range of several celldiameters from the decaying atom.

Within this range however, the cytotoxicity of α-particles is extraordinary. This may be contributed to the high linear energy transfer (100 keV/$\mu$m) and the high electrical charge of the particles. At doses of 100 to 200 cGy α-radiation may be 5 to 100 times as toxic as γ-or β-radiation.

Such a radioimmunoconjugate has been disclosed in Macklis et. al. (Science vol. 240 p1024-1026, 1988) wherein a $^{212}$Bismuth isotope is used, coupled to a monoclonal antibody by the cyclic anhydrid of DTPA (Diethylenetriamine pentaacetic acid), a derivative of the well-known chelating agent DTPA.

The monoclonal antibody described is directed against a murine antigen represented as Thy 1.2, which is present on the surface of both normal and malignant murine T-cells.

Bismuth isotopes have also been described in U.S Pat. No. 4.454.106 for the purpose of radioimmunotherapy.

Another α-particles emitting isotope mentioned for use in immunotherapy is $^{211}$Astatine (Bloomer et. al. Science vol. 212 p340-341, 1981).

$^{212}$Bismuth has a physical half-life of 60.55 minutes and $^{211}$Astatine has a physical half-life of just over seven hours.

A short physical half-life like that of Bismuth requires a very fast extraction of the isotope from its source, a very fast chelation step (including the removal of adventitiously bound metal) and the extraction must be followed by immediate administration. Every hour delay between obtaining the isotope and administering it results in a dosage which is only half the intended dose.

It is therefore necessary that the source for radioactive bismuth is available in the direct vicinity of the patient. The source described for $^{212}$Bismuth is either $^{228}$Thallium, $^{224}$Radium, or $^{212}$Pb. The first two decay chains involve a $^{220}$Rn isotope, which is a noble gas and may easily leak away. Most hospitals will not be equipped to house a source with such risks. $^{212}$Pb of course has a much too short physical half-life (10 hours) to enable a producer to achieve a good distribution.

$^{211}$Astatine has a longer physical half-life than $^{212}$Bismuth. It would perhaps be possible to locate the source for this isotope outside the hospital. However, Astatine is a halogen atom which behaves very similar to Iodine, including the well known drawbacks of accumulation in certain organs and tissues. Especially because $^{211}$Astatine compounds are unstable in vivo (Int. J. Appl. Rad. Isotop.32 p. 913 1981).

Apart from these drawbacks there is also the problem of obtaining sufficient quantities of the aforementioned isotopes, because their sources are available only in microgram quantities if at all.

The present invention provides a novel radioimmunoconjugate which includes a radionuclide which overcomes the previous mentioned problems.

Another problem arising in the field of radioimmunotherapy in humans is the availability of suitable antibodies. Murine antitumor antibodies which have been suggested, will, especially after several administrations, give rise to an immunereaction by the patient. Even fragments of these antibodies will eventually lead to this response.

The solution to this problem would be the use of human monoclonal antibodies, but these are not readily available.

A good method of obtaining human monoclonal antibodies has been disclosed in European Patent Application No. 0151030. However, this method tends to produce IgM-antibodies primarily.

A problem with IgM-antibodies is that they are fairly slow in reaching the site in the body where their antigens are located (the tumor). This may take from a day up to several days.

Therefore the normally used α-emitters such as the earlier mentioned, will have decayed for the larger part when they reach their site of action.

Among a list of others, $^{225}$Actinium has been suggested as a suitable α-emitter (Monoclonal Antibodies Drug Dev.;Proceedings of the John Jacob Abel Symposium for Drug Dev.,1982, page 159-171).

The α-emitter of interest according to the authors, is 224Ra.

The paper relates to mouse IgG-monoclonals or fragments thereof, which localize faster than human IgM-antibodies, but which will lead to an immuneresponse.

Furthermore, the authors did not try any α-emitters in therapy, but only tried 125I-IgG-conjugates in a model system.

The conjugates with $^{125}$I did not lead to any improved results over unlabeled antibodies in their experiments.

Later on the authors turned from $^{224}$Ra with a half-life of approximately three days to $^{212}$Bi, which has an even shorter half-life.

SUMMARY OF THE INVENTION

The invention resides in a conjugate comprising $^{225}$Actinium or one of its daughters as a radionuclide and a slowly localizing human-or humanized antibody.

Slowly localizing antibodies are mean to include slowly localizing fragments of antibodies, or fragments that have been made slowly localizing by associating them with a carrier.

In choosing $^{225}$Actinium a radionuclide is provided with a suitable physical half-life of approximately ten days.

This matches the localization time of human IgM-antibodies very well.

Furthermore a practically inexhaustible source is available in $^{233}$Uranium, which is abundantly stockpiled as an unused source of fuel for nuclear breeder reactors.

DETAILED DESCRIPTION OF THE EMBODIMENTS

From $^{233}$Uranium $^{229}$Thorium can be extracted, which can be used as an intermediate source (physical half-life 7340 years). Moreover, the decay chain of $^{225}$Actinium, represented below, includes four decays via an emission of α-particles, without producing significant amounts of X-rays and no halogen atoms or noble gas isotopes.

This cascade may significantly increase the cytotoxic effect on the tumor cells.

However, upon the first decay the remaining isotope may be propelled away from the tumor (or into the tumor, for that matter!). This would result in emission of α-particles in places far away from the tumor. The physical half-lifes of $^{221}$Fr and $^{217}$At, as well as $^{213}$Po, are too short for these isotopes to wander far off, but the $^{213}$Bi has a physical half-life which may result in displacement of the isotope.

Therefore the present invention also provides a pharmaceutical composition comprising a radioimmunoconjugate including $^{225}$Actinium or one of its daughters as well as one or more scavenging agents.

Scavenging agents are usually free chelating agents which may bind the wandering isotopes. In doing so they prohibit the isotopes to invade organs or tissues and improve the speed with which the isotopes are excreted.

The chelating agents used to bind Actinium or Bismuth, as well as the agents used as scavengers may be the usual chelating agents such as DTPA or derivatives thereof, PLED or its derivatives, EDTA or its derivatives, or crownethers or derivatives etc.

As scavengers EDTA, 2,3-dimercaptosuccinic acid and penicillamine are preferred.

Scheme. 1

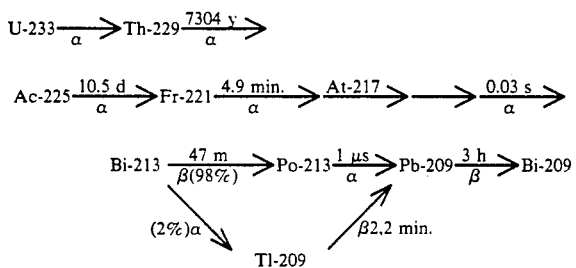

An additional advantage of using $^{225}$Actinium is that its compatibility with specific antibodies and chelating agents can be easily tested by substituting $^{227}$Actinium for $^{225}$Actinium.

$^{227}$Actinium is a commercially available β-emitter with a relatively long physical half-life, which, from a chemical point of view behaves similar to $^{225}$Actinium.

The tumorspecificity of the antibodies used in the radioimmunoconjugates according to the invention is of course a very important parameter. The best results will be obtained with antibodies which bind to the surface of the tumor cells. Internalization is not necessary, because the kinetic energy of the α-particles, as well as the rebounce energy of the isotope is high enough to have a cytotoxic effect from the outside.

Suitable antibodies are those obtained by the method disclosed in European Patent Application No. 0151030.

The dose range over which the $^{225}$Actinium can be used effectively without causing too many side-effects is highly dependent on the kind of therapeutic use which is intended. Presently the intended use will mostly be adjuvant therapy (right after surgery, in order to attack micrometastases) and treatment of localized tumors. The invention will be illustrated in the following experimental part.

EXAMPLES

Extraction of Thorium-229 from Uranium-233 built u from Thorium-232 in thermal or epithermal neutron power reactors This exercise, mainly performed in different places in the world during the fifties, has led to a stock-pile of Uranium-233, intended as a fission material for thermal power reactors.

Pursuit of this development has been largely abandoned, at least for the time being. Throughout the years, substantial amounts of Thorium-229 did build up through alpha decay from Uranium-233 and can therefore be isolated from stock-piles. The extraction and purification chemistry is sufficiently known and does not need any further elaboration. More than sufficient amounts of Thorium-229 are available in the world from this route to serve the cancer therapy market for the forthcoming thousands of years. Thorium-229, obtained from this route, and because of its radio-active decay halflife in the order of 8000 years, will serve as a source material for a "cow" from which AC-225 can be extracted on a continuous or intermittent basis. One gram of Thorium-229 can be recovered by this means form about 10 kg of Uranium-233, 30 years of age.

Another means of obtaining Thorium-229 is irraadiation of Radium-226 in a thermal high flux reactor for about 3 years. About 20 grams of Radium-226 is needed to obtain 1 gram of Thorium-229 by this route Much chemistry has been developed in the period of the nineteen sixties and seventies, to enable the separation and purification of Thorium from Uranium, c.q. Thorium from Radium, etc. Quite a lot of detailed literature is available. Some major references are (amongst many others):

I. Brandsstetz, Soviet Radiochem. 5, 660 (1963).

Gmelin Handbook of Inorg. Chem. U, Vol. D4 (1983), and U, Vol. D3 (1982).

Proceedings of Actinide/Lanthanide Separations, Honolulu 1984 (Ed. G.R. Chappin, World Scientific).

A.T. Kandil, Radiochim. Acta 26, 63 (1979).

2. Using Thorium-229 as a "cow" for the production of AC-225

The continuous or batch-wise separation of Ac-225 from Thorium-229 and decay products is a well-known, straight forward extraction procedure. Well-known extraction media/solvents are TTA, TBP, HDEHE and sodiumthiocyanide, with or without using $CCl_4$ as a co-solvent. These, but also a variety of other methods, have been extensively described in the literature during the 60's and the 70's. One gram of Thorium-229 produces 100 microgram per year of AC-225, assuming a 100% net extraction yield. This is equivalent to 5 curies per annum of Ac-225 α-radioactivity.

Literature (a selection of a long list):

P.C. Stevenson: "The Radiochemistry of the Rare Earths, Sc, Y and Ac, (US Report NAS-NS 3020 (1961))

N.W. Kinley: Progr. Nucl. Energy, Ser. IX 8, 89 (1967)

P.M. Eagle: Preliminary Report of the Actinium Separation Project, US-Report MLM-454 (1950).

M. Allison, Nucleonics 12, 32 (1954)

J. Tousset Thesis, French Report NP-13367 (1961)

A. M. Poshausen, J. Inorg. Nucl. Chem. 16, 323 (1961)

R.A. Day, J.Am. Chem. Soc. 72, 5662 (1950).

3. Radio-therapeutic effectiveness of MeV-range α-rays

The radiosensitivity of a population of tumor cells is often expressed by $D_0$, the inverse slope of the linear portion of the logarithmic survival curve. For α particles the logarithmic survival curves and known values of radiobiological sensitivity (i.e., the $D_0$ is known) the dose required to reduce the cell population to any level of cell survival can be computed from the equation:

$$D = -(D_0)(\ln S)$$

where S is the fraction of surviving cells (Humm and Cobb, J. of Nucl. Med., 31-1, 75 (1990)). Uniform distribution of the o particle source materials through tumor material is assumed. Typical valueas of $D_0$ for α particles are between 50–100 rad. The estimated fraction of tumor cells surviving in an absorbed dose of 350 rad, for $D_0 = 75$ rad, is 0.01 or 1%.

The following table, derived from the formula given above, gives the survival ratio of tumor cells (or for that matter any equally sensitive biological cells) as a function of different radiation doses:

| | |
|---|---|
| 700 rad | gives a survival ratio of 0.01% |
| 500 rad | gives a survival ratio of 0.1% |
| 350 rad | gives a survival ratio of 1% |
| 15 rad | gives a survival ratio of 82% |
| 10 rad | gives a survival ratio of 88% |
| 5 rad | gives a survival ratio of 93% |
| 1.5 rad | gives a survival ratio of 98% | all assuming a value for $D_0$ of 75 rads, as is generally thought to be the case for alpha ray doses.

Assuming a homogenuous distribution of Ac-225 through a tumor mass, a tumor size large in comparison with the average penetration range of α-rays through biological cell material (in the order of 75 microns at most), and a characteristic penetration range of radioactive decay recoil nuclea through the cell tissue of the order of 1000 Å, and furthermore taking into account that 4 α's are emitted through the Ac-225 decay chain within a relatively short duration, it is assumed that the total α decay-related energy is dissipated within the tumor mass. From that it can be calculated that 1 μCi of Ac-225 per gram tumor together with its daughters will then supply a dose of 750 rad of energy to the tumor material, inducing a killing ratio of 99,99% of tumor cells.

It depends on the size of a tumor to what extent the assumptions given above are fully true: the larger the tumor, the smaller the chance the Actinium is homogeneously distributed throughout the tumor before decay; the smaller the tumor, the larger the chance of decay energy not fully absorbed by tumor cells. For example, it can be calculated that for an Actinium atom on the surface of a one-cell tumor, the amount of total decay energy generated being absorbed by the tumor cell will be in the order of only 250 rad per μCi on a gram basis Like always in pharmacology, also in the case of α-radioimmunotherapy the challenge of supplying sufficient active material to those locations relevant for effectiveness of therapy, in comparison to body tissue at large, is the key for the size or the extent of the "therapeutic range" In the case of α-emitting Ac-225 isotopes conjugated onto human monoclonal antibodies, the therapeutic range is solely determined by the nature and properties of the antibodies: their relative affinity to the tumor cell surface antigens for which they are destined in comparison with their affinity to other human body tissues, and the relative duration of the antibody-antigen bond in comparison with the average retention time of the antibodies by the other body tissue.

4. Affinity and clearance rate data of human monoclonal antibodies against colon tumor cell surface antigens Reference M.G. Hanna, Jr. PhD, et al: "Development and Application of Human Monoclonal Antibodies", current status and future directions in immunoconjugates University of Miami - School of Medicin, continuing education series, Feb. 15–16, 1990. Biotechnology Research Institute of Organon Teknika Corporation Rockville, MD 20850, developed human monoclonal antibodies of the IgM-type, with specific affinity for human colon carcinoma cells (cytoplastic and cell surface determinants). These antibodies referred to as 28A 32 and 16.88 were labeled with Iodine-131 (5mCi/8 μg) and intravenously administered to patients with metastic colorectal carcinoma. The antibodies can be repeatedly and stably grown on a kg scale and repeated administration to the patients showed that they are not immunogenic.

Relevant for the present patent application are the observations made by radio-active imaging regarding the pharmacokinetic characteristics of these antibodies. Day to day scanning of the patients showed 5 to 7 days after intravenous administration. The average retention time in imaged nodules showed to be 17 days.

An important conclusion of these observations is that the retention time of conjugated antibodies in tudor tissue is at least 3 times as long as the average retention time in other body tissues.

In addition, prechirurgical pharmacokinetic studies were completed in several colon cancer patients and tumor versus normal colon ratios have been obtained for the human MAb 16.88 The results demonstrated tumor to normal tissue uptake ratios (liver metastases) of up to 10 to 1. Simular results were achieved by R.P. McCabe, et al (cancer research 48, 4348–4353, August 1, 1988) on colorectal cancer bearing nude mice, this time using Iodine-125-labeled antibody.

The conclusion is that, using such antibodies, an α-ray dose to onco-colorectal cells in patients can be achieved in the order of a factor 25 or more higher than to body tissue in general of such patients In other words, an administration of over 350 rad of Ac-225-induced α-rad energy per gram of tumor tissue can be achieved by the administration of about 15 rad/g to the overall body tissue. This implies that an administration of Ac-labeled monoclonal antibody causing 99% kill of tumor cells will only induce an 18% kill of non-tumor tissue cells.

On this basis, and recalling that 1μCi of Ac-225 delivers 750 rad of radiation energy to one gram of biological tissue, such a "therapeutic range" for a patients of 75 kg of body weight can be achieved by post-operative administration of 1.5 mCi of Ac-225conjugate. This corresponds with a "therapeutic dose" of about 30 ng of Actinium-225 p.m.: This implies that 100,000 patients per annum can be treated with such a therapeutic dose on the basis of 3 mg per annum of Ac225, which, with an overall efficiency of about 30%, can be continuously extracted from a "cow" containing 100 grams of Thorium-229.

Any improvement in selectivity of antibody above the FIGURES given in this example will directly, in proportion, reduce the need of the size of the Thorium-229 "cow".

EXAMPLE Ia (4-isothiocyanatobenzyl)-DTPA 2,5 mg/ml is dissolved in 7 PBS (0,066 M phosphate/ 0,13 M NaCl pH=7,2–7,4) and 10 μl of this solution are added to the monoclonal antibody dissolved in PBS (1 mg/ml). The mixture is stirred for two hours at ambient temperature. Free chelating agent is removed by size exclusion filtration over sephadex G50 (25 cm×0,5 cm) in PBS. The chelator-antibody conjugate is stored in PBS at 4° C. in a concentration of 0,5 mg/ml.

EXAMPLE Ib

The volume of the $^{225}$Ac as eluted from the $^{225}$Ac generator (100 μCi) is reduced to 50 μl and the pH is adjusted to 5 with NaH2phosphate-solution (0,1 M). The resulting solution is incubated immediately with (benzyl) DTPA-conjugated antibody: 250 μg in 0, 5 ml pBS for 15 minutes. DTPA (1 mg) in 10 μl PBS are added and the mixture is incubated for another 5 minutes. The mixture is subjected to size exclusion chromotography over sephadex G50 (10×2 cm) and the void volume (yield 80%) gives $^{225}$Ac-benzyl-DTPA-monoclonal antibody.

EXAMPLE II

A solution of $^{225}$Ac (100μCi) as obtained from the cow (in HCl) was evaporated to dryness under a gentle stream of nitrogen. It was dissolved in 100 μl PBS buffer. To this solution 500 μl antibody (16.88) conjugated to benzyl DTPA (2mg/ml) was added and after 10 minutes incubation at room temperature the mixture was chromatographed over a Sephadex$^R$ PD10 column using PBS as element. The high molecular weight fractions were collected and used (as such) or after concentration by centrifugation over Centricon® pretreated with BSA.

We claim:

1. A radiommunoconjugate, comprising a radionuclide that emits α-particles, a chelating agent and an antibody specific for a tumor associated antigen, wherein the radionuclide is $^{225}$Actinium or a mixture of $^{225}$Actinium and at least one of its daughters, and wherein said antibody is selected from the group consisting of a human monoclonal antibody and a humanized antibody.

2. A radioimmunoconjugate according to claim 1, wherein the antibody is an IgM-antobody.

3. A radioimmunoconjugate according to claim 2, wherein the antibody is monoclonal antibody 16.88.

4. A radioimmunoconjugate according to claim 2, wherein the antibody is monoclonal antibody 28A32.

5. Pharmaceutical composition comprising a radioimmunoconjugate according to claim 1 and a pharmaceutically acceptable carrier.

6. Pharmaceutical composition according to claim 5, comprising at least one scavenging agent.

* * * * *

(12) REEXAMINATION CERTIFICATE (4450th)
United States Patent
Geerlings et al.

(10) Number: US 5,246,691 C1
(45) Certificate Issued: Oct. 9, 2001

(54) RADIOIMMUNOTHERAPY USING α-PARTICLES EMISSION

(75) Inventors: Maurits W. Geerlings, Rozendaal; Franciscus M. Kaspersen, Heesch, both of (NL)

(73) Assignee: Akzo N.V., Arnhem (NL)

Reexamination Request:
No. 90/005,214, Dec. 21, 1998

Reexamination Certificate for:
Patent No.: 5,246,691
Issued: Sep. 21, 1993
Appl. No.: 07/657,580
Filed: Feb. 19, 1991

(30) Foreign Application Priority Data

Jun. 19, 1989 (EP) .............................. 89.201591.8
Jun. 19, 1990 (WO) .................................. PCT/EP90/00990

(51) Int. Cl.$^7$ .................................. A16K 43/00
(52) U.S. Cl. .......................... 424/1.53; 424/1.49; 534/10
(58) Field of Search ...................... 530/391.3; 424/178.1, 424/179.1, 181.1, 1.49

(56) References Cited

U.S. PATENT DOCUMENTS 5,428,154  6/1995  Gansow et al. .

OTHER PUBLICATIONS

Lambrecht, "Radionuclide Generators," Radiochimica Acta 34, 9–24 (1983), R. Oldenbourg Verlag, Munich. p. 19.

Spitsyn & Mikheev, "Generators for the Production of Short–Lived Radioisotopes," Atomic Energy Review, vol. 9, No. 4, pp 787 et seq. (1971), International Atomic Energy Commission, Vienna. pp. 820–823.

Riechmann et al, "Reshaping human antibodies for therapy," Nature 332, 323–327 (1988), Macmillan Magazines, London.

*Primary Examiner*—Long V. Le

(57) ABSTRACT

The present invention relates to the use of Actinium or one of its daughters in radioimmunotherapy. Also provided are immunoconjugates comprising an isotope, a chelating agent and a slowly localizing antibody. The invention also includes pharmaceutical compositions comprising said immunoconjugates, as well as such compositions comprising one or more scavenging agents. The compositions according to the invention are particularly useful for the treatment of micrometastases in adjuvant therapy, as well as for treatment of localized tumors.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–6 is confirmed.

* * * * *